United States Patent [19]

Huc et al.

[11] Patent Number: 5,071,436
[45] Date of Patent: Dec. 10, 1991

[54] SUBSTITUTE BONY MATRIX PRODUCTS PROMOTING OSTEOGENESIS

[75] Inventors: Alain Huc, Sainte-Foy-Les-Lyon; Roland Allard, Saint Chamond; Jacques Bejui, Lyons, all of France

[73] Assignee: Societe Anonyme Bioetica, Lyons, France

[21] Appl. No.: 701,607

[22] Filed: May 14, 1991

Related U.S. Application Data

[63] Continuation of Ser. No. 574,383, Aug. 27, 1990, abandoned, which is a continuation of Ser. No. 462,844, Dec. 29, 1989, abandoned, which is a continuation of Ser. No. 223,686, Jul. 22, 1988, abandoned, which is a continuation of Ser. No. 892,097, Jul. 30, 1986, abandoned.

[30] Foreign Application Priority Data

Jul. 30, 1985 [FR] France .............................. 85 12053

[51] Int. Cl.$^5$ ............................................. A61F 2/28
[52] U.S. Cl. ......................................... 623/16; 623/66
[58] Field of Search ................... 623/1, 16, 66, 18, 11

[56] References Cited

U.S. PATENT DOCUMENTS

| | | | |
|---|---|---|---|
| 4,060,081 | 11/1977 | Yannas et al. | 623/66 X |
| 4,350,629 | 9/1982 | Yannas et al. | 128/DIG. 8 X |
| 4,451,397 | 5/1984 | Huc et al. | 128/DIG. 8 X |
| 4,623,553 | 11/1986 | Ries et al. | 623/18 X |

OTHER PUBLICATIONS

*Hackh's Chemical Dictionary* 4th Ed.; McGraw-Hill Book Co., 1969, p. 172.

*Primary Examiner*—David J. Isabella
*Assistant Examiner*—Debra S. Brittingham
*Attorney, Agent, or Firm*—Herbert Dubno; Jonathan Myers

[57] ABSTRACT

A new composition is disclosed which serves as a substitute for the bony matrix material present in bones. The new composition includes an association of collagen-hydroxy-apatite and a glycosaminoglycan. The concentration of the hydroxyapatite is preferably 15 to 25% and the concentration of the glycosaminoglycan is between 1 and 2% per liter of 1% collagen gel. The biomaterial product is useful in applications in reconstructive orthopedic surgery as a substitute for natural bone matrix material.

5 Claims, No Drawings

SUBSTITUTE BONY MATRIX PRODUCTS PROMOTING OSTEOGENESIS

This is a continuation of co-pending application Ser. No. 07/574,383 filed on 27 Aug. 1990 now abandoned which is a cont. of Ser. No. 07/462,844 filed 29 Dec. 1989 now abandoned which is a cont. of Ser. No. 07/223,686 filed July 1988, which is a cont. of Ser. No. 06/892,097 filed 30 July 86 now abandoned.

FIELD OF THE INVENTION

The present invention relates to a substitute bony matrix product which promotes osteogenesis

BACKGROUND OF THE INVENTION

The loss of primary or secondary bony substance has always posed reconstruction problems for the orthopedic, reconstructive surgeon. Replacement parts for the entire bone system are not available in inexhaustible supply even if certain portions can be removed from donors without causing mechanical damage; e.g. the iliac crest, the epiphyses and metaphyses involving the thigh bone and the tibia for example.

The bone banks containing human or animal bone pose application technique problems and accordingly materials obtained from the bone banks have not always functioned satisfactorily. Accordingly, effort has been made to seek out substitute materials, more or less of organic origin. The materials can be either permanent or temporary. In the former case, the use of such materials results in a cellular colony, and these colonies have an initial mechanical resistance that is not negligible and resemble coral.

In the latter case, what is formed are bone-like tissues having the ability to take on the mechanical and histological characteristics of bone tissue with time and the given spacial requirements.

OBJECT OF THE INVENTION

The present invention has its object to provide a biomaterial belonging to the second abovementioned category, in which a composition is produced amounting to a bony matrix which has the ability to promote osteogenesis in the treatment of traumatized tissues where loss of bony material has occurred.

It is a further object of the invention to provide a synthetic bony material stitchery similar to bone and having the ability to promote osteogenesis.

SUMMARY OF THE INVENTION

It is known that bone is composed of rigid conjunctive tissues and includes bone cells and a extracellular matrix. The matrix is constituted essentially of collagen fibers, proteoglycans, and minerals. The protein part principally contains type 1 collagen, very reticulated. This significant reticulation makes impossible total extraction of the collagen without first carrying out an enzymatic attack. The mucopolysaccharide portion is composed essentially of acidic chondroitine-4-sulfate acid. The mineral part contains about 85% hydroxyapatite, calcium carbonate, and small quantities of calcium and magnesium fluorides. This matrix has two functions: first of all a mechanical role of support, secondly a biological role in the location of the existence as well as the development of the bone cells, that is the osteoblasts.

Interesting experiments (Hayashi et al, Arch. Orthop. Traumat. and Surg., 99, pp 265-269, 1982) have already been carried out in this field based upon a mixture of collagen-hydroxyapatite, and it can be stated that this biomaterial induces a greater osteogenic effect than collagen itself. It is necessary to note that this material always contains some cavities. Above all, collagen, native or dereticulated, is sensitive to attack by collagenases, and is degraded in the organism.

On the other hand very often collagen of animal origin is utilized for construction of biomaterials utilized in human therapy.

Although the immunogenic effect of collagen is very low, especially when it possesses the helicoidal structure, the employment in human applications of a protein of a different animal species, can still result in rejection by a host organism.

It is known furthermore that the glycosaminoglycans play an important role in the migration and the cellular proliferation as well as in the biosynthetic activity of the cells (I. Yannas, G. Skover, and D. Michaeli).

The present applicants have been able to determine in addition that the biodegradability and the immunogenicity of the collagen can essentially be diminished by the utilization of glycosaminoglycans bonded to the collagen by dehydrothermic reticulation.

The replacement product having a bony matrix facilitates osteogenesis according to the invention and is indeed a new biomaterial constituted by the association of collagen-hydroxy-apatite and glycosaminoglycans. Preferably the concentration of the glycosaminoglycans is between 1 and 2% per liter of 1% collagen gel. An even more preferred product has the concentration of the hydroxyapatite and the collagen to each be about equal, which is six times greater than the concentration of glycosaminoglycan component.

The product according to the invention is advantageously in the form of a sponge, the preparation of which is described in the non-limiting examples.

EXAMPLE 1

Preparation of a sponge comprising dereticulated collagen-acidic chondroitin-4-sulfate-hydroxyapatite.

(a) Preparation of dereticulated collagen

Veal hides obtained from freshly slaughtered calves are first washed with water and mashed for 1 hour in a fuller apparatus.

The hair and subcutaneous tissues are separated from the hide with the help of a splitting apparatus having a rotating blade.

The recovered skin is chopped and ground. The ground material is washed in three successive baths with a phosphate buffer at a pH of 7.8. Between each bath the ground material is separated from the solution by centrifuging continuously at 4000 rpm. The residue is rinsed in two successive baths of deionizing water and the liquid is separated from the ground material in the same fashion as in the previous washing operation. The first treatments serve to eliminate the noncollagenous substances. The tissue is then placed in a vat containing an NaOH solution at a pH of 14. After agitation for about half an hour, the material is then allowed to stand for about 8 hours. The mixture is then acidified with hydrochloric acid to a pH of 2. Then NaCl is added to the mixture until it reaches a concentration of 10%. The precipitated collagen is then dialyzed with the sterile, deionized water.

(b) Preparation of the acidic chondroitin-4-sulfate

The acid is extracted from the nasal septa of calves. The septa are first of all washed carefully with a solution of sodium chloride, nine parts per thousand. They are then chopped and ground. The ground material is then added at the rate of 1 kg/liter to a solution of 0.5 N potassium hydroxide. After agitation the mixture is washed and allowed to stand for 24 hours at ambient temperature. At the end of this time period, the supernatant liquid is separated from the insoluble material be centrifuging at 30,000 g for 30 minutes. Then pure acetic acid is added to the supernatant to neutralize the alkali. The solution is then concentrated five times by vacuum evaporation. The concentrate is poured into 3 times its volume of ethanol. The precipitate, removed by decantation, is dissolved in deionized water. The recovered acidic chondroitin-4-sulfate is obtained by lyophilization of the solution.

(c) Preparation of hydroxyapatite

Two volumes (V) of a solution of 0.5 M $CaCL_2$ and 0.5 M $Na_2HPO_4$ are poured under agitation at equal rates into a beaker. The formed precipitate is decanted and washed four times with a volume 2V of water. The suspension is diluted in a volume 2V of distilled water and to it is added in a proportion of 100 ml per 4 liters, of a freshly prepared solution of 40% NaOH. The mixture is maintained at the boiling point for 1 hour. After decantation the supernatant liquid is eliminated. The recovered precipitate is washed 4 timed with water. A sodium phosphate buffer of 0.01 M is added at a pH of 6.8 to the precipitate and the resulting suspension is brought to a boil. After decantation the supernatant is eliminated and buffer is freshly added. The suspension is then maintained under a boil for 5 minutes. After decantation the precipitate is maintained at a boil in the same buffer for 15 minutes followed by two treatments with 0.001 M solution of the phosphate buffer. After eliminating the water the hydroxypatite is obtained in the form of a powder.

(d) Preparation of the mixture and obtaining the sponge 20 g of apatite and 1.6 g of acidic chondroitin-4-sulfate are placed in a liter of an atelocollagenic gel (1%) in distilled water at a pH of 6.5. After homogenization, the mixture is poured in a pan, then lyophilized. The lyophilizate is then broken up into small pieces having dimensions of 35×20×10 mm. The sponges thus obtained are dried under a vacuum of 0.1 mm of Hg for 48 hours at 80° C.

EXAMPLE 2

Preparation of sponges containing native collagen-acidic chondroitin-4-sulfate-hydroxyapatite (a) Preparation of a homogeneous collagen suspension Veal hides obtained from freshly slaughtered calves are first of all washed with water and mashed for 1 hour in a fuller apparatus. The hair and subcutaneous tissue are separated from the skin with the help of a splitting apparatus having a rotating blade.

The recovered skin is chopped and ground. The ground material is washed in 3 successive baths with a phosphate buffer at a pH of 7.8. Between each bath the ground material is separated from the solution by centrifuging continuously at 4000 rpm. The residue is rinsed in 2 successive baths of deionized water and the liquid is separated from the ground material in the same fashion as in the previous operation. The tissue is then placed in a solution of acetic acid. The concentration of the collagen in this solution must be 10% and that of the acid 40% with respect to the collagen.

The paste obtained is then diluted with sterile, distilled water in such a fashion as to obtain a 3% collagen solution. This new preparation is homogenized in a grinder of the type Ultra-Turrax.

(b) The preparation of the acidic chondroitin-4-sulfate is obtained according to the product of Example 1.

(c) The preparation of the hydroxyapatite is carried out according to the same conditions as in Example 1.

(d) Preparation of the mixture and obtaining the sponge

To the collagen gel are added 3 g of solid hydroxyapatite and the glycosaminoglycans, the final concentration of the collagen being identical to that of the hydroxyapatite and 6 times greater than than of the glycosaminoglycans. After agitation of a minimum duration of 1 hour, the mixture is centrifuged. The residue is then placed in a pan or other acceptable container and lyophilized. The hardness of the obtained material varies directly in proportion to the velocity and duration of the centrifugation.

Product Tests

Testing on animals have been carried out, using a model (sample) of experimental pseudoarthrosis. The tests consisted in removing 20 to 25 mm portions of the femur from dogs and to fill in the space created with the aid of several samples of the biomaterial to be tested. The rigidity of the assembly is ensured by a metallic plate fastened to the separated bone segments. Some of the dogs have been subjected to a drilling of the large trochanter with the aid of a drill and a cutter in order to be able to implant a piece of marrow obturator, consisting of collagen acido-soluble hydroxyapatite and of glycosaminiglycan. Other dogs have served as a control group. For, this purpose, they have received an implant to replace the lost dyaphisary substance of the spongy bone removed from the homolateral iliac crest. The space where the bone has been removed was filled with samples of atelocollagen hydroxyapatite glycosaminoglycan complex. The animals were sacrificed at time intervals varying between 1 and 6 months after the implant of these samples.

The results of these tests have shown that no acute inflammatory reaction was caused by the biomaterials and that no immune reaction has been caused by the collagen. A filling of the lost bone substance has been noted and, in certain cases, a bone graft with a homogeneously dense radiological aspect and histologically, with a genuine ossification front was found.. Furthermore, the samples seem to preclude the formation of fibrosis scary tissue which in the long run opposes the consolidation, by progressive substitution. Finally, they avoid the formation of a pseudoarthrosis if the junction between bone and biomaterial remains rigid. The above described biomaterial is of great interest for orthopedic and reconstructive surgery.

What is claimed is:

1. An osteogenesis-promoting spongy biomaterial for use in a mammalian organism, said material having the ability to facilitate osteogenesis and to take on the mechanical and histological characteristics of bone tissue with time and given spacial requirements, said biomaterial being a composition consisting essentially of glycosaminoglycans bonded to collagen by dehydrothermic reticulation, together with hydroxyapatite so that bonding in said composition is solely by dehydrothermic reticulation.

2. The osteogenesis-promoting spongy biomaterial defined in claim 1 wherein the collagen is dereticulated collagen.

3. The osteogenesis-promoting biomateiral defined in claim 1 wherein the concentration of hydroxyapatite is 20 g/l of 1% collagen gel and the concentration of the glycosaminoglycan is 1.6 g/l of 1% collagen gel.

4. The osteogenesis-promoting biomaterial defined in claim 1 wherein the glycosaminoglycan is acidic chondroitin-4-sulfate.

5. The osteogenesis-promoting biomaterial defined in claim 1 wherein the collagen is dereticulated collagen, the concentration of hydroxyapatite is 20 g/l of 1% dereticulated collagen gel, and the concentration of the glycosaminoglycan is 1.6 g/l of 1% dereticulated collagen gel.

* * * * *